(12) United States Patent
Jensen et al.

(10) Patent No.: US 11,452,480 B2
(45) Date of Patent: Sep. 27, 2022

(54) DEVICE AND METHOD FOR ASSESSING THE LEVEL OF CONSCIOUSNESS, PAIN AND NOCICEPTION DURING WAKEFULNESS, SEDATION AND GENERAL ANAESTHESIA

(71) Applicant: Quantium Medical SL, Mataro (ES)

(72) Inventors: Erik Weber Jensen, Sant Pol de Mar (ES); Joan Fontantet, Sabadell (ES); Mathieu Jospin, Mataro (ES)

(73) Assignee: Quantium Medical SL, Mataro (ES)

( * ) Notice: Subject to any disclaimer, the term of this patent is extended or adjusted under 35 U.S.C. 154(b) by 993 days.

(21) Appl. No.: 15/744,558

(22) PCT Filed: Apr. 7, 2016

(86) PCT No.: PCT/DK2016/000012
§ 371 (c)(1),
(2) Date: Jan. 12, 2018

(87) PCT Pub. No.: WO2017/012622
PCT Pub. Date: Jan. 26, 2017

(65) Prior Publication Data
US 2018/0206784 A1    Jul. 26, 2018

(30) Foreign Application Priority Data
Jul. 17, 2015   (DK) .......................... PA 2015 00420

(51) Int. Cl.
*A61B 5/04*   (2006.01)
*A61B 5/00*   (2006.01)
(Continued)

(52) U.S. Cl.
CPC .......... *A61B 5/4821* (2013.01); *A61B 5/0536* (2013.01); *A61B 5/369* (2021.01);
(Continued)

(58) Field of Classification Search
CPC ... A61B 5/4821; A61B 5/0536; A61B 5/0042; A61B 5/7257; G16H 50/20; G06T 2207/30016
See application file for complete search history.

(56) References Cited

U.S. PATENT DOCUMENTS

| | | | |
|---|---|---|---|
| 7,228,169 B2 | 6/2007 | Viertio-Oja et al. | |
| 7,725,173 B2 | 5/2010 | Viertio-Oja et al. | |

(Continued)

FOREIGN PATENT DOCUMENTS

| | | |
|---|---|---|
| CN | 104545949 | 4/2015 |
| WO | WO 2012/010173 A1 | 7/2011 |

(Continued)

OTHER PUBLICATIONS

Chan, M. et al. "BIS-Guided Anesthesia Decreases Postoperative Delirium and Cognitive Decline." Journal of Neurosurgical Anesthesiology. Jan. 2013. pp. 33-42, vol. 25(1).

(Continued)

*Primary Examiner* — Christian Jang
(74) *Attorney, Agent, or Firm* — Cook Alex Ltd.

(57) ABSTRACT

The present invention disclosed a device and method for assessing in real time the hypnotic and analgesic effect in a subject during wakefulness, sedation and general anaesthesia via drug interactions and physiological signals. In a preferred embodiment of the present invention, the analgesic and hypnotic effect of drug(s) infused in a subject could be accurately assessed in real time through the device and method disclosed in the present invention, comprising steps of receiving data from electroencephalography (EEG) device, receiving data from brain impedance tomography device, obtaining pharmacodynamic and pharmacokinetic parameters of drug(s) infused in the subject, defining initial indices of consciousness and nociception as a function of said EEG and brain impedance tomography data, and gen- (Continued)

erating output of final indices of consciousness and nociception in real time from processing input of EEG, brain tomography and drug interaction data using established mathematical manipulation.

13 Claims, 12 Drawing Sheets

(51) Int. Cl.
*A61B 5/0536* (2021.01)
*G16H 50/20* (2018.01)
*A61B 5/369* (2021.01)
*G16H 20/10* (2018.01)

(52) U.S. Cl.
CPC .......... *A61B 5/4839* (2013.01); *G16H 50/20* (2018.01); *A61B 5/0042* (2013.01); *A61B 5/4824* (2013.01); *A61B 5/7257* (2013.01); *G06T 2207/30016* (2013.01); *G16H 20/10* (2018.01)

(56) References Cited

U.S. PATENT DOCUMENTS

| | | | |
|---|---|---|---|
| 7,725,174 B2 | 5/2010 | Kern et al. | |
| 7,925,338 B2 | 4/2011 | Huiku | |
| 2006/0122523 A1 | 6/2006 | Bonmassar et al. | |
| 2006/0217628 A1* | 9/2006 | Huiku | A61B 5/4839 600/544 |
| 2008/0021345 A1 | 1/2008 | Kern et al. | |
| 2011/0295096 A1* | 12/2011 | Bibian | A61B 5/7221 600/372 |
| 2012/0016215 A1* | 1/2012 | Condurso | G16H 70/00 600/316 |
| 2012/0150059 A1 | 6/2012 | Bonmassar et al. | |
| 2012/0277548 A1 | 11/2012 | Burton | |
| 2013/0150748 A1 | 6/2013 | Jensen | |
| 2013/0331660 A1 | 12/2013 | Et | |
| 2015/0038940 A1 | 2/2015 | Kreuer | |
| 2015/0164413 A1 | 6/2015 | Wu et al. | |
| 2018/0000409 A1 | 1/2018 | Jensen et al. | |

FOREIGN PATENT DOCUMENTS

| | | |
|---|---|---|
| WO | WO 2012/010173 | 1/2012 |
| WO | WO 2014/091291 A1 | 12/2013 |
| WO | WO 2014/091291 | 6/2014 |
| WO | WO 2015/086020 | 6/2015 |
| WO | WO 2016/095918 | 6/2016 |

OTHER PUBLICATIONS

Jang, J. "ANFIS: Adaptive-Network-Based Fuzzy Inference System." IEEE Transactions on Systems, Man, and Cybernetics. May/Jun. 1993. pp. 665-685, vol. 23(3).
Jensen, E.W. et al. "Monitoring Hypnotic Effect and Nociception with Two EEG-Derived Indices, qCON and qNOX, During General Anaesthesia." 2014. pp. 933-941, vol. 58(8).
Kang, G.T. and Sugeno, M. "Structure Identification of Fuzzy Model." Fuzzy Sets and Systems. 1988. pp. 15-33, vol. 28.
Kurth, S. et al. "Mapping of Cortical Activity in the First Two Decades of Life: A High-Density Sleep Electroencephalogram Study." Oct. 6, 2010. pp. 13211-13219, vol. 30(40).
Pollard, B.J. et al. "Functional Electrical Impedance Tomography by Evoked Response (fEITER): Sub-second Changes in Brain Function During Induction of Anaesthesia with Propofol." Euro. J. of Anaesthesiology. Jun. 2011. pp. 97-98, vol. 28.
Sandin, R. "Awareness 1960-2002, Explicit Recall of Events During General Anaesthesia." Advances in Experimental Medicine and Biology. 2003. pp. 135-147, vol. 523.
Sandin, R. et al. "Awareness During Anaesthesia: A Prospective Case Study." The Lancet. Feb. 26, 2000. pp. 707-711, vol. 355.
Schwender, D. et al., "Conscious Awareness During General Anaesthesia: Patients' Perceptions, Emotions, Cognition and Reactions." British Journal of Anaesthesia. 1998. pp. 133-139, vol. 80.
Struys, M. et al. "Ability of the Bispectral Index, Autoregressive Modelling with Exogenous Input . . . " Anesthesiology. 2003. pp. 802-812, vol. 99(4).
Takagi, T. and Sugeno, M. "Fuzzy Identification of Systems and Its Applications to Modeling and Control." IEEE Transactions on Systems, Man, and Cybernetics. Jan./Feb. 1985. pp. 116-132, vol. SMC-15(1).
Wackermann, J. and Matousek, M. "From the 'EEG Age' to a Rational Scale of Brain Electric Maturation." Electroencephalography and Clinical Neurophysiology. Jun. 5, 1998. pp. 415-421, vol. 107(6).
European Intl Search Report for PCT/DK2016/000012 dated Oct. 10, 2016.
Supp European Intl Search Report for EP 16827290 dated Jan. 16, 2019.

\* cited by examiner

A

B

DEVICE AND METHOD FOR ASSESSING THE LEVEL OF CONSCIOUSNESS, PAIN AND NOCICEPTION DURING WAKEFULNESS, SEDATION AND GENERAL ANAESTHESIA

CROSS-REFERENCE TO RELATED APPLICATIONS

The present application is a U.S. national stage application of International Patent Application No. PCT/DK2016/000012, filed Apr. 7, 2016, which claims the benefit of and priority to Danish Patent Application No. PA 2015 00420, filed Jul. 17, 2015, both of which are incorporated by reference herein in their entireties.

FIELD OF THE INVENTION

The present invention generally relates to assessing the level of consciousness, pain and nociception in a patient.

BACKGROUND OF THE INVENTION

Anesthesia is defined as a drug induced state where the patient has lost consciousness, loss of sensation of pain or response to any other stimuli. To obtain these objectives, the anesthesiologist can use different classes of drugs, mostly hypnotics and analgesics. This allows the patients to undergo surgery and other procedures without the distress and pain they would otherwise experience.

The state of analgesia for surgery is reached by the administration of analgesics. The demand of analgesics varies for each patient. Therefore there is a need for continuous preferably non invasive monitoring of the analgesia effect in the patient. Nociception and the perception of pain define the need for analgesia to obtain pain relief. Autonomic responses such as tachycardia, hypertension, emotional sweating and lacrimation, although non-specific, are regarded as signs of nociception and consequently inadequate analgesia.

When administering enough doses of hypnotics, the following loss of consciousness make that the patient does not perceive the stimuli, but the neurovegetative and somatic responses are not necessarily abolished. When administering enough doses of analgesics they block the nociceptive stimuli and prevent the neurovegetative and somatic responses. However, they do not always produce a loss of consciousness and amnesia.

Anesthesia is a dynamic process where the effects of the anesthetic drugs are counteracted by the intensity of the different stimuli. When this equilibrium is broken, the patient could evolve to a different anaesthetic depth, without the anesthesiologist being aware of it. The overall incidence of intraoperative awareness with recall is about 0.2-2%, but it may be much higher in certain high risk patients like multiple trauma, caesarean section, cardiac surgery and haemodynamically unstable patients. Sometimes the patients could remember voices or even noises. In other cases the patients cannot move and advice to the anesthesiologist that they are awake or are in pain during surgical maneuvers. This is a complication that can lead to severe postoperative psychosomatic dysfunction in almost 50% of the patients. (Br J Anaesth 1998; 80:133-39). As intraoperative awareness could be a major medico-legal liability to the anesthesiologists and could lead to postoperative psychosomatic dysfunction in the patients, it should therefore be avoided. (Lancet. 2000; 355:707-11; Adv Exp Med Biol. 2003; 523:135-47). Recently it has been shown that the postoperative cognitive dysfunction was increased in patients where anaesthetics were overdosed (J Neurosurg Anesthesiol. 2013; 25(1):33-42).

One of the objectives of modern anesthesia is to ensure adequate level of consciousness to prevent awareness without inadvertently overloading the patients with anesthetics, which might cause increased postoperative complications. There are several widely used clinical methods for assessing the level of consciousness during general anaesthesia, including the Observers Assessment of Alertness and Sedation Scale (OAAS) and Ramsey Sedation Scale. However, the disadvantages of using clinical scales in the operating room are that they cannot be used continuously and that they are cumbersome to perform. Furthermore, they require the patient's collaboration, which in some cases might be difficult, for example infants. This has led to the investigation into automated assessment of the level of consciousness.

Recently, some automatic devices have arrived on the market to provide an objective quantification of the level of consciousness of the patient. The most prevailing method is the analysis using the electroencephalogram (EEG) where a scalp EEG is recorded and subsequently processed by an algorithm which maps EEG signal into an index, typically in a range of 0 to 100. EEG based method is well-established for assessing brain activity by recording and analyzing the weak biopotential signals generated in the cortex of the brain with electrodes attached on the skin of the skull surface. It has been in wide use for decades in basic research of the neural systems of the brain, as well as in clinical diagnosis of various neurophysiological diseases and disorders.

However, EEG signal alone could not provide an accurate assessment of aesthetic state of a patient, multiparameter approach is proposed in some patents as shown below.

U.S. Pat. No. 7,228,169 disclosed a method and apparatus combining EEG and electromyography (EMG) for determining the cerebral state of a patient with fast response.

U.S. Pat. No. 7,925,338 described a system monitoring the hypnotic effect and analgesia effect by using EEG, pharmacokinetic and pharmacodynamics models, and also a cardiovascular function.

Therefore, there is a long felt and unmet need for improved systems and methods for accurately assessing the level of consciousness, pain and nociception in patients in real time during wakefulness, sedation and general anaesthesia. The present invention is intended to comply with all these needs.

SUMMARY OF THE INVENTION

It is one object of the present invention to provide a device (100) for assessing in real time the hypnotic and analgesic effect in a subject during wakefulness, sedation and general anesthesia, comprising at least one processor and at least one computer readable medium coupled to the processor, said at least one computer readable medium comprises operations executed by said at least one processor. The operations are:
  a. receiving electroencephalography (EEG) data;
  b. receiving drug interaction data of drug infused in said subject;
  c. defining an initial index of consciousness (qCON) as a function of said EEG data and said second set of data;
  d. defining an initial index of nociception (qNOX) as a function of said EEG data and said second set of data;
  e. providing final index of consciousness (qCON') and final index of nociception (qNOX'). It is within the scope of the present invention that said processor is configured to calculate said index of consciousness (qCON(')) and said index of nociception (qNOX(')) in real time using established mathematical manipulation from input of said EEG data, said second set of brain function data and said drug interaction data.

It is another object of the present invention to provide the device as defined above, said operations further comprising receiving a second set of data on state of brain function from a brain impedance tomography device.

It is another object of the present invention to provide the device as defined above, wherein said brain impedance tomography is measured from the same electrodes as said EEG positioned on said subject's forehead.

It is another object of the present invention to provide the device as defined above, wherein indices qCON and qNOX are derived from a function of at least one parameter selected from EEG spectra, energy ratios extracted by a fast fourier transform, standard deviation of Energy in EEG frequency band, rate of burst suppression, brain impedance, plethysmographic curve or any combination thereof.

It is another object of the present invention to provide the device as defined above, wherein said infused drug has a group of effects consisting of: anesthetic, hypnotic, analgesic, or any combination thereof.

It is another object of the present invention to provide the device as defined above, wherein said drug interaction data including a group consisting of: pharmacokinetic data, pharmacodynamic data or any combination thereof.

It is another object of the present invention to provide the device as defined above, wherein said mathematical manipulation is selected from a group consisting: a linear regression, a logistic regression, a fuzzy logic classifier, a neural network, an Adaptive Neuro Fuzzy Inference System (ANFIS), a quadratic equation or any combination thereof.

It is another object of the present invention to provide the device as defined above, wherein value of hypnotic index qCON(') varies from 0 to 100, corresponding to level of consciousness.

It is another object of the present invention to provide the device as defined above, wherein value of nociception index qNOX(') varies from 0 to 100, corresponding to a probability of response to noxious stimuli.

It is another object of the present invention to provide the device as defined above, wherein final indices qCON' and qNOX' are optimized from qCON and qNOX respectively, by including a group of parameters consisting of: analgesics parameters, hypnotics parameters, analgesic interaction, age, brain age or any combination thereof.

It is another object of the present invention to provide the device as defined above, further comprising a reference scale developed based on a group consisting of: OAAS scale, Ramsay scale, effect site concentration of drug, end tidal concentration of the volatile gases, response or lack of response to noxious stimulation or any combination thereof.

It is another object of the present invention to provide the device as defined above, further comprising a warning module configured for activating an alarm if the least mean square (LMS) difference between the hypnotic or analgesic effect assessed by the drugs pharmacodynamics (pharmacodynamics=PD) and that assessed by qCON or qNOX is greater than set threshold; said LMS is expressed as:

$$LMS_{pain\ level} = \sum_{t=1}^{N} (qNOX_t - PDpain_t)^2$$

$$LMS_{hyp} = \sum_{t=1}^{N} (qCON_t - PDhyp_t)^2$$

where $PD_{pain}$ is the pain level assessed by the pharmacodynamics, $PD_{hyp}$ is the hypnotic effect assessed by the pharmacodynamics of the drugs administered to the patient.

It is another object of the present invention to provide the device as defined above, wherein prediction of wake-up time after stopping anaesthetics is provided.

It is another object of the present invention to provide a method for real time assessment of the hypnotic and analgesic effect in a subject during wakefulness, sedation and general anesthesia. The method comprising steps of:
  a. receiving electroencephalography (EEG) data;
  b. receiving drug interaction data infused in said subject;
  c. defining an initial index of consciousness (qCON) as a function of said EEG data and said second set of data;
  d. defining an initial index of nociception (qNOX) as a function of said EEG data and said second set of data;
  e. providing final index of consciousness (qCON') and final index of nociception (qNOX').

It is within the scope of the present invention that said index of consciousness (qCON(')) and said index of nociception (qNOX(')) is calculated in real time via at least one processor using established mathematical manipulation from input of said EEG data, said second set of brain function data and said drug interaction data.

It is another object of the present invention to provide the method as defined above, further comprising a step of receiving a second set of data on state of brain function is obtained through a brain impedance tomography device.

It is another object of the present invention to provide the method as defined above, wherein said brain impedance tomography is measured from the same electrodes as said EEG positioned on said subject's forehead.

It is another object of the present invention to provide the method as defined above, wherein indices qCON and qNOX are derived from a function of at least one parameter selected from EEG spectra, energy ratios extracted by a fast fourier transform, standard deviation of Energy in EEG frequency band, rate of burst suppression, brain impedance plethysmographic curve or any combination thereof.

It is another object of the present invention to provide the method as defined above, wherein said infused drug has a group of effects consisting of: anesthetic, hypnotic, analgesic, or any combination thereof.

It is another object of the present invention to provide the method as defined above, wherein said drug interaction data including a group consisting of: pharmacokinetic data, pharmacodynamic data or any combination thereof.

It is another object of the present invention to provide the method as defined above, wherein said mathematical manipulation is selected form a group consisting: a linear regression, a logistic regression, a fuzzy logic classifier, a neural network, an Adaptive Neuro Fuzzy Inference System (ANFIS), a quadratic equation or any combination thereof.

It is another object of the present invention to provide the method as defined above, wherein value of hypnotic index qCON(') varies from 0 to 100, corresponding to level of consciousness.

It is another object of the present invention to provide the method as defined above, wherein value of nociception index qNOX(') varies from 0 to 100, corresponding to a probability of response to noxious stimuli.

It is another object of the present invention to provide the method as defined above, wherein final indices qCON' and qNOX' are optimized from qCON and qNOX respectively, by including a group of parameters consisting of: analgesics parameters, hypnotics parameters, analgesic interaction, age, brain age or any combination thereof.

It is another object of the present invention to provide the method as defined above, further comprising a reference scale developed based on a group consisting of: OAAS scale, Ramsay scale, effect site concentration of drug, end tidal concentration of the volatile gases, response or lack of response to noxious stimulation or any combination thereof.

It is another object of the present invention to provide the method as defined above, further comprising a warning module configured for activating an alarm if the least mean square (LMS) difference between the hypnotic or analgesic effect assessed by the drugs pharmacodynamics (pharmacodynamics=PD) and that assessed by qCON or qNOX is greater than set threshold; said LMS is expressed as:

$$LMS_{pain\ level} = \sum_{t=1}^{N}(qNOX_t - PDpain_t)^2$$

$$LMS_{hyp} = \sum_{t=1}^{N}(qCON_t - PDhyp_t)^2$$

where $PD_{pain}$ is the pain level assessed by the pharmacodynamics, $PD_{hyp}$ is the hypnotic effect assessed by the pharmacodynamics of the drugs administered to the patient.

It is another object of the present invention to provide the method as defined above, wherein prediction of wake-up time after stopping anaesthetics is provided.

It is another object of the invention to provide a device (100) for assessing in real time the hypnotic and analgesic effect in a subject during wakefulness, sedation and general anesthesia, comprising at least one processor and at least one computer readable medium coupled to the processor, said at least one computer readable medium comprises operations executed by said at least one processor, said operations are:
  a. receiving electroencephalography (EEG) data;
  b. receiving drug interaction data of drug infused in said subject;
  c. defining an initial index of nociception (qNOX) as a function of said EEG data and said second set of data;
  d. providing final index of nociception (qNOX');
wherein said processor is configured to calculate said index of nociception (qNOX(')) in real time using established mathematical manipulation from input of said EEG data and said drug interaction data.

It is another object of the invention to provide a method for assessing in real time the hypnotic and analgesic effect in a subject during wakefulness, sedation and general anesthesia, comprising steps of:
  a. receiving electroencephalography (EEG) data;
  b. receiving drug interaction data infused in said subject;
  c. defining an initial index of nociception (qNOX) as a function of said EEG data and said second set of data;
  d. providing final index of nociception (qNOX');
wherein said index of nociception (qNOX(')) is calculated in real time via at least one processor using established mathematical manipulation from input of said EEG data and said drug interaction data.

It is another object of the invention to provide a device (100) for assessing in real time the hypnotic and analgesic effect in a subject during wakefulness, sedation and general anesthesia, comprising at least one processor and at least one computer readable medium coupled to the processor, said at least one computer readable medium comprises operations executed by said at least one processor, said operations are:
  a. receiving electroencephalography (EEG) data;
  b. receiving drug interaction data of drug infused in said subject;
  c. defining an initial index of consciousness (qCON) as a function of said EEG data and said second set of data;
  d. providing final index of consciousness (qCON');
wherein said processor is configured to calculate said index of consciousness (qCON(')) in real time using established mathematical manipulation from input of said EEG data and said drug interaction data.

It is another object of the invention to provide a method for assessing in real time the hypnotic and analgesic effect in a subject during wakefulness, sedation and general anesthesia, comprising steps of:
  a. receiving electroencephalography (EEG) data;
  b. receiving drug interaction data infused in said subject;
  c. defining an initial index of consciousness (qCON) as a function of said EEG data and said second set of data;
  d. providing final index of consciousness (qCON');
wherein said index of consciousness (qCON(')) is calculated in real time via at least one processor using established mathematical manipulation from input of said EEG data and said drug interaction data.

BRIEF DESCRIPTION OF THE FIGURES

For a better understanding of the invention and to show how the same may be carried into effect, specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In the accompanying drawings.

DETAILED DESCRIPTION OF THE PREFERRED EMBODIMENTS

Figure 1:
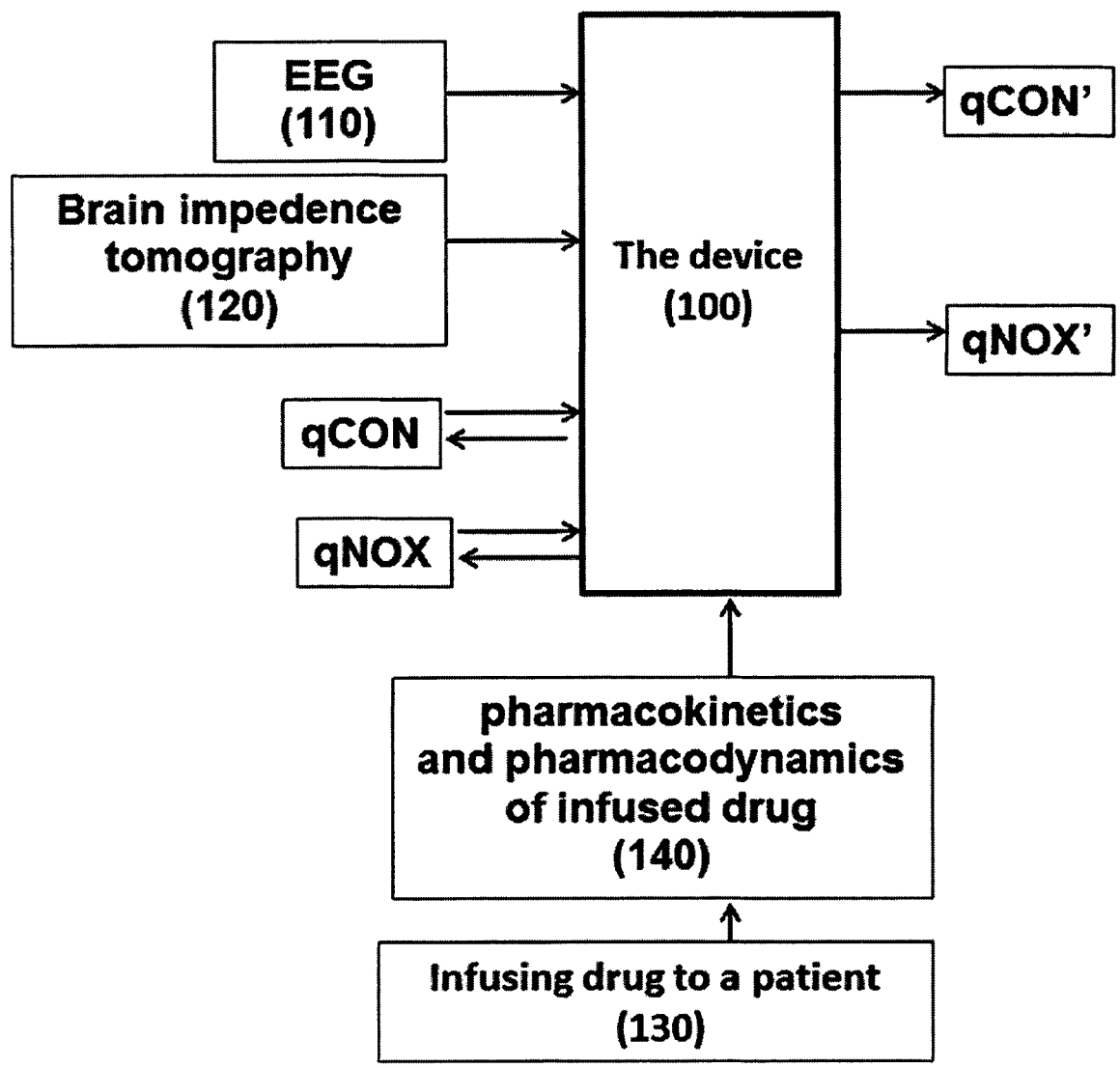
FIG. 1 is a schematic illustration of output of the indices qCON(') and qNOX(').

The following description is provided, alongside all figures of the present invention, so as to enable any person skilled in the art to implement said invention and sets forth the suitable examples of carrying out this invention. The invention is applicable to other embodiments or being practiced or carried out in various ways. It is also to be understood that the terminology employed herein is for the purpose of description and should not be regarded as limiting.

U.S. Pat. No. 7,725,173 discloses a method and apparatus for measuring the responsiveness of a subject with a lowered level of consciousness. In this system, the EEG signal measured from a patient is digitized, filtered to exclude high and low frequency artifacts and processed as sets of 5 second time windows or "epochs". The processing method calculates the high-frequency power of the EEG signal, defined as the power in a band extending from 20 Hz to 35 Hz within a single epoch, and stores the calculated value. This calculation is repeated for each epoch producing a time series (known as the first measure), which is the high-frequency EEG power in each epoch. The processing method then calculates a change variable indicative of the changes in the high-frequency EEG power. The process first finds the minimum value within the preceding 1 minute of the first measure. The change variable is then determined by subtracting the minimum value of the first measure from the current value of the first measure. Finally, a responsiveness index is calculated by averaging successive values of the logarithm of the change variable over 30 minutes. The responsiveness index is indicative of the mean/cumulative high-frequency EEG power changes with respect to time. The application teaches that other measures may be used instead of high-frequency EEG power as the first measure, such as EEG entropy or measures based on fractal spectrum analysis, Lempel-Ziv complexity, or bispectral or multi spectral analyses or the bispectral Index.

Brain impedance tomography was described previously by Pollard B J (Euro J Anaesthesiology 2011(28): 97-98). It provides a new imaging technique that sheds light into human consciousness. Several publications (Anesthesiology 2003; 99(4):802-12) demonstrated effect site concentrations of drugs (e.g. propofol and remifentanil) could be combined with an EEG derived index in order to generate a more precise index of the level of consciousness.

PCT Application No. WO2012010173 disclosed an apparatus for the on-line identification of drug effect using drug interactions and physiologic signals, in particular the interaction between anesthetics and analgesics combined with the EEG for precise assessment of the level of consciousness in awake, sedated and anaesthetized patients. Effect site concentrations of propofol and remifentanil are fed as inputs into a model. In contrast, a method according to some embodiments of the present invention, additionally or alternately, uses inputs of hypnotics parameters and analgesics parameters, which can include several different parameters from the infusion. These new parameters could be, but not limited to, infusion speed, variation of infusion speed, total amount infused, integral and derivative of amounts infused over a time window. Using inputs of hypnotics parameters and analgesics parameters can provide increased precision of the final output.

PCT Publication WO 2014/091291 A1 discloses a method for determining probability of response to pain and nociception of a subject during different levels of arousal. The method includes utilizing input from an EEG sensor to calculate an index of nociception. In contrast, a method of some embodiments of the present invention, additionally or alternatively, receives input of drug interaction data of drug infused in a subject, and the calculation of index of consciousness and index of nociception includes drug interaction data. Calculating the index of consciousness and index of nociception using drug interaction data can provide an increased precision of the final indices.

Figure 12:
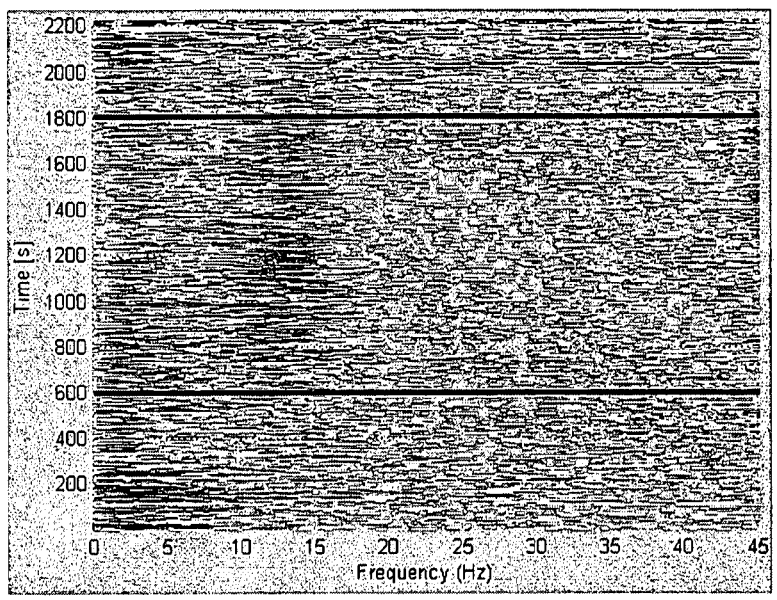
FIG. 12 shows the time frequency plot of the frontal EEG from a subject of 19 years (a) and a subject of 84 years (b). On FIG. 12a the subject was anaesthetized from 600 to 1800 s.
Figure 12:
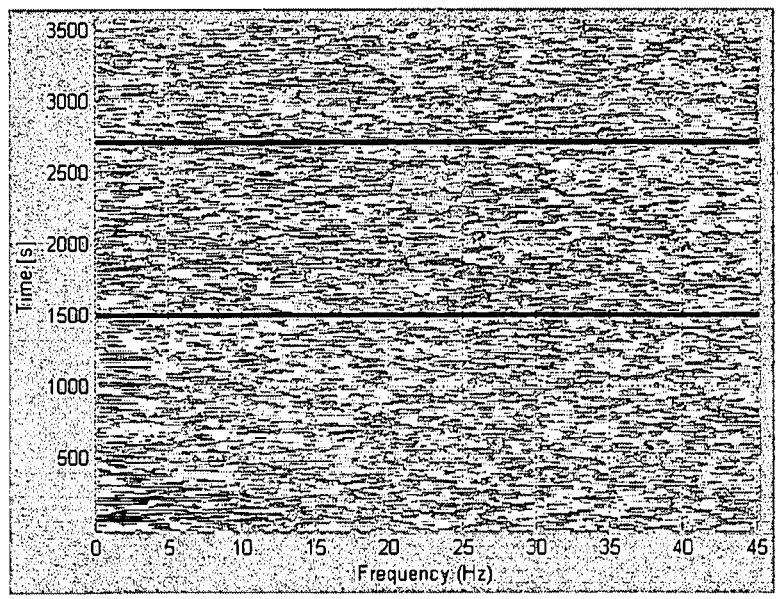

In the present invention, a combination of parameters of EEG, brain impedance tomography, pharmacokinetics and pharmacodynamics of drugs are employed. There are publications (J Neurosci. Oct. 6, 2010; 30(40): 13211-13219) suggesting that there is change in EEG data related to subjects' age, typically the EEG energy is lowered. Thus there is need to develop method of quantitative assessment of EEG age-related changes and incorporate the age parameter into EEG data (Electroencephalogram Clin Neurophysiol. 1998; 107(6):415-21). So in the present invention, the age and brain age are also used as an input to generate the final indices of consciousness and nociception. With increasing age the total energy and the energy in the alpha band is decreased as shown in FIG. 12. In particular the decrease in energy in the alpha band (10-15 Hz) during anaesthesia between the young (FIG. 12a) and the elderly (FIG. 12b) can be used to compensate the value of the energy in the alpha band before entering the parameter to the classifier. On the other hand, if, EEG data of the patient is available before the anaesthesia is started then the patient can be classified to a particular age group, possibly different from the real age, this term is called "brain age". This a priory knowledge can be used to know which level of alpha waves would be expected during anaesthesia. The objective of the present invention is to provide a safe apparatus and method using multiparameter approach for assessing in real time hypnotic and analgesic effect of drug(s) in the patient during wakefulness, sedation and general anaesthesia.

The term "brain impedance tomography" refers hereinafter to the electrical impedance tomography of brain function, the signal is recorded from the same electrodes as the EEG device. There are a variety of devices, processors and systems for the acquisition and processing of brain tomography data.

The term "qCON" refers hereinafter to an index of level of consciousness; the value varies from 0 to 100 and is standardized, corresponding to level of consciousness from low to high.

The term "qCON'" refers hereinafter to the final version of qCON; the value varies from 0 to 100 and is standardized, corresponding to level of consciousness from low to high.

The term "qNOX" refers hereinafter to an index of nociception; the value varies from 0 to 100 and is standardized, corresponding to probability of response to noxious stimuli from low to high.

The term "qNOX'" refers hereinafter to the final version of qNOX; the value varies from 0 to 100 and is standardized, corresponding to probability of response to noxious stimuli from low to high.

The term "brain age" refers hereinafter to the age corrected for certain EEG behaviours.

The term "drug" refers hereinafter to any kind of at least one substance or medicament which has anaesthetic, analgesic or hypothetic effect. The anaesthetic and hypnotic drug(s) could be administered orally, by pumps, by injector, by inhaler, by vaporizers or any combination thereof.

The term "fast Fourier transform (FFT)" refers hereinafter to an algorithm to compute the discrete Fourier transform (DFT) and its inverse. A Fourier transform converts time (or space) to frequency and vice versa; an FFT rapidly computes such transformations. As a result, fast Fourier transforms are widely used for many applications in engineering, science, and mathematics.

The term "Observers Assessment of Alertness and Sedation Scale (OAAS)" refers hereinafter a clinical scale to evaluate the level of consciousness during general anesthesia as shown in the table below:

| Score | Responsiveness |
|-------|---------------|
| 5 | Responds readily to name spoken in normal tone. |
| 4 | Lethargic response to name spoken in normal tone. |
| 3 | Responds only after name is called loudly or repeatedly. |
| 2 | Responds only after mild prodding or shaking. |
| 1 | Responds only after noxious stimuli. |
| 0 | No response after noxious stimuli. |

The term "Ramsey Sedation Scale" refers hereinafter a clinical scale to evaluate the level of consciousness during general anesthesia as shown in the table below as shown in the table below:

| Score | Responsiveness |
|-------|---------------|
| 6 | No response to light glabellar tap or loud auditory stimulus |
| 5 | Sluggish response to light glabellar tap or loud auditory stimulus |
| 4 | Brisk response to light glabellar tap or loud auditory stimulus |
| 3 | Responsive to commands only |
| 2 | Cooperative, oriented, tranquil |
| 1 | Anxious, agitated, restless |

Figure 2:
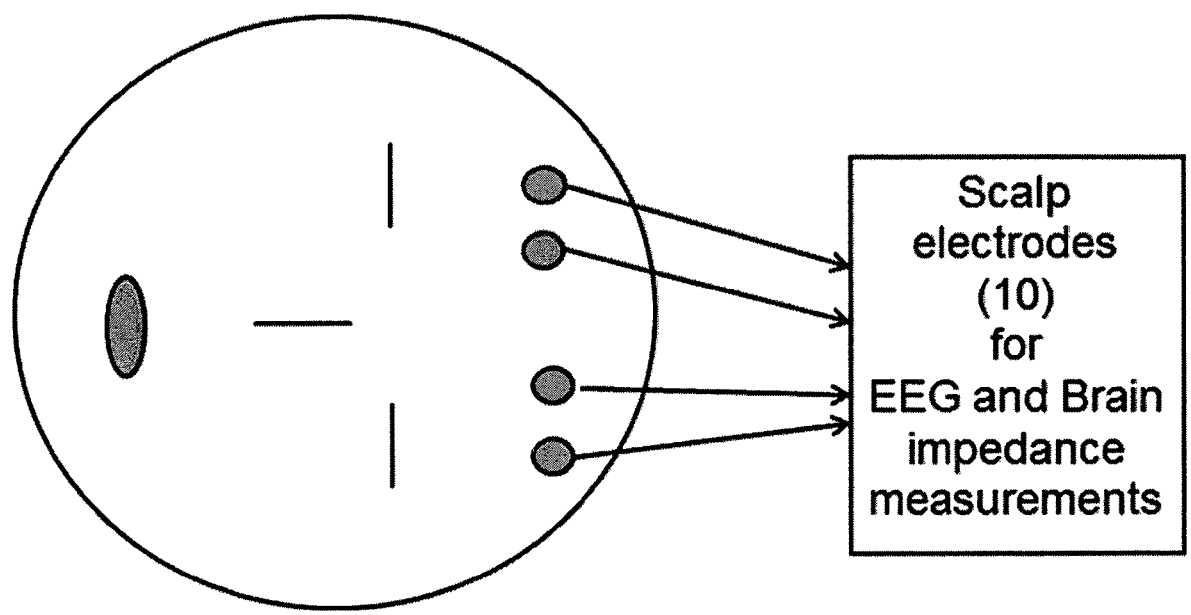
FIG. 2 is a representative diagram of positions of the electrodes in the forehead of a subject.

Reference is now made to FIG. 1, which shows the schematic illustration of output of the indices of level of consciousness qCON(') and indices of level of nociception qNOX(') from the device (100) and method disclosed in the present invention. One or multiple channel EEG (110) and brain impedance tomography are recorded (120) from four scalp electrodes (10) positioned left, middle and right on the forehead of a subject (FIG. 2). The EEG (110) and the impedance tomography (120) together with the data from pharmacokinetics and pharmacodynamics (140) of the infused drug are all used as input to the device (100) comprising at least one processor and at least one computer readable medium coupled to the processor. The device (100) accurately assesses in real time the hypnotic and analgesic effect of the infused drug in the subject during wakefulness, sedation and general anesthesia, through steps of: a) receiving data from EEG (110); b) receiving data from brain impedance tomography device (120); c) obtaining pharmacodynamic and pharmacokinetic parameters of drug(s) infused in the subject; d) defining initial indices of consciousness qCON and nociception qNOX as a function of said EEG and brain impedance tomography data; and e) providing output of final indices of consciousness qCON' and nociception qNOX' in real time from processing input of EEG, brain tomography and drug interaction data using established mathematical manipulation. The mathematical manipulation could be a linear regression, a logistic regression, a fuzzy logic classifier, a quadratic equation a neural network or a hybrid between a fuzzy logic system and a neural network such as an Adaptive Neuro Fuzzy Inference System (ANFIS). The qNOX assumes low values if the patient does not respond to noxious stimuli and high values if the patient is responding.

According to one embodiment of the present invention, the pharmacokinetics and the pharmacodynamics parameters of the infused drugs are input to the processing module. The parameters could be amount of drugs infused, in total or in a set time window, the derivative(s) of the drugs infused, the plasma concentration, and the effect site concentration assessed by the Schneider model, Minto model or a model using an Adaptive Neuro Fuzzy Inference System (ANFIS).

According to another embodiment of the present invention, the mathematical model based on ANFIS is used for the development of both qCON and qNOX. ANFIS is a hybrid of an artificial neural network and a fuzzy logic system, and was developed by Jang in 1993 (IEEE Trans on Systems, Man and Cybernetics 1993, 23:665-685.) It represents a Sugeno-type fuzzy system in a special five-layer feed-forward network architecture where the inputs are not counted as a layer. The first order Sugeno fuzzy model was originally proposed by Takagi and Sugeno in 1985 (IEEE Trans. on Systems, Man and Cybernetics, 1985; 15:116-132) and further elaborated by Sugeno and Kang in 1988 (Structure identification of fuzzy models. 1988; 28:15-33).

Standard learning procedures from neural network theory are applied in ANFIS. Back propagation is used to learn the antecedent parameters, i.e. the membership functions; least squares estimation is used to determine the coefficients of the linear combinations in the rules' consequents. An epoch in the learning procedure has two passes. In the first pass, which is the forward pass, the input patterns are propagated, and the optimal consequent parameters are estimated by an iterative least mean squares procedure, while the antecedent parameters are fixed for the current cycle through the training set. In the second pass, which is the backward pass, the patterns are propagated again. In this pass, back propagation is used to modify the antecedent parameters, while the consequent parameters remain fixed. This procedure is then iterated through the desired number of epochs. If the antecedent parameters are initially chosen appropriately, based on expert knowledge, then one training epoch will be sufficient. This is because the least mean square (LMS) algorithm determines the optimal consequent parameters in one pass. Furthermore, if the antecedents do not change significantly by use of the gradient descent method, the LMS calculation of the consequents will not lead to another result through successive epochs.

According to another embodiment of the present invention, a Fast Fourier Transform (FFT) is applied to the EEG and the energy in frequency bands is defined. Subsequently the ratios are calculated which are used as input to the processing module. The Burst Suppression (BS) and standard deviation of the EEG amplitude in a frequency band and time window are used as well.

The burst suppression (BS) is extracted from the time domain of the EEG (110) and a FFT is carried out on the EEG which enables the calculation of the energy in distinct frequency bands. This is has been disclosed in Jensen E W et al. "Monitoring hypnotic effect and nociception with two EEG derived indices, qCON and qNOX, during general anaesthesia" (Acta Anaesthesiol Scand. 2014; 58(8):933-41).

A new element has been added to the algorithm, which is the standard deviation of the logarithm to the energy of frequency bands (for example, 5-40 Hz) during a time window. It is used as an input to the processing module as well. Calculation of said standard deviation is described in the following paragraph.

The power in a frequency band, Pn (for example, 5-40 Hz) is measured and the logarithm is calculated, termed Log(Pn). The standard deviation (SD) of n consecutive values of Log(Pn) is calculated. This value is termed SDPn. Smoothing is then carried out, defining $$SDPn\_old=(1-\alpha)\times SDPn\_old+\alpha\times SDPn \quad (1)$$

where n is an integer in the range of 5 to 100, typical value of n is 10; and a is in the range of 0 to 1, typical value of $\alpha$ is 0.03. The SDPn_old is estimate of the morphology of the EEG before Burst Suppression occurs. This is characterized by periods of low amplitude EEG followed by bursts, however the low amplitude EEG is not as suppressed as during burst suppression, hence this morphology is termed near burst suppression (NBS).

The SDPn_old is then an input to the processing module, typically an ANFIS or a multiple logistic regression.

According to another embodiment of the present invention, initial indices of consciousness qCON and nociception qNOX are defined as a function of said EEG data, the device (100) provides output of final indices of consciousness qCON' and nociception qNOX' in real time from processing input of EEG and drug interaction data using established mathematical manipulation. The mathematical manipulation could be a linear regression, a logistic regression, a fuzzy logic classifier, a neural network or a hybrid between a fuzzy logic system and a neural network such as an Adaptive Neuro Fuzzy Inference System (ANFIS).

Figure 3:
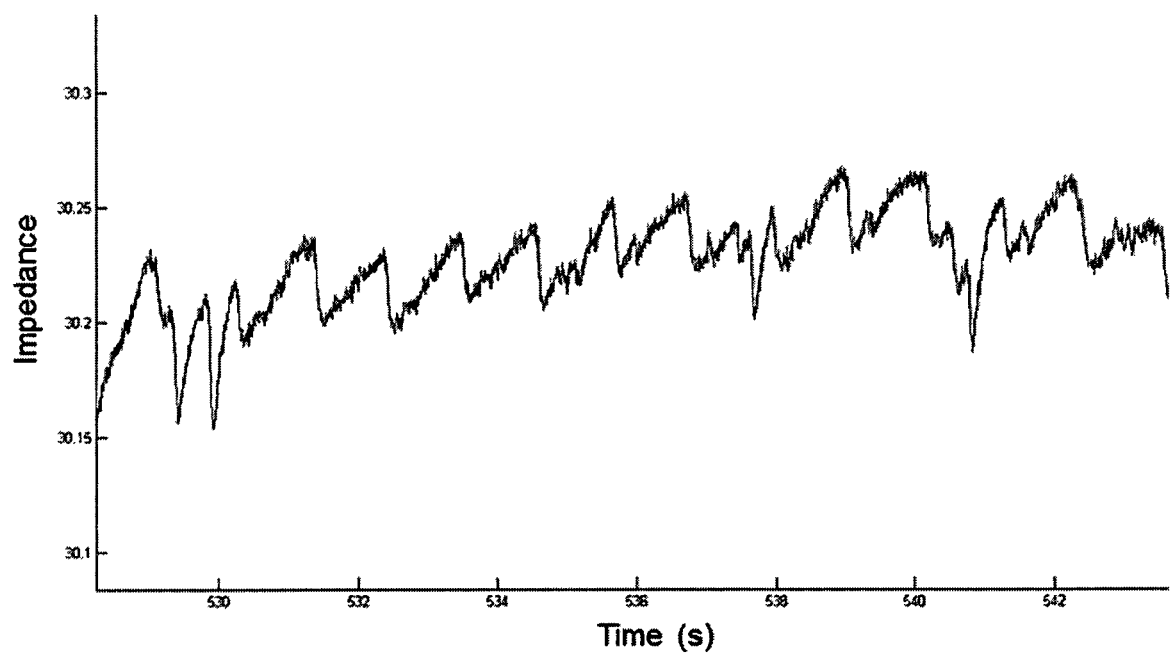
FIG. 3 is an example of the brain impedance plethysmographic curve.

According to another embodiment of the present invention, the impedance is measured from the same electrodes as the EEG (as shown in FIG. 2). The impedance changes as a function of anesthesia. The brain impedance tomography curve on its own is a correlate to the brain blood flow, the amplitude and the derivative of the plethysmographic curve is proportional to the brain blood flow, this is shown in the recent patent application by Jensen E W (Denmark Patent Application No. 201500062). The brain flow will typically decrease during anaesthesia, but could also decrease due to loss of blood or because of vasospasms which could occur in the ICU. An example of the brain impedance tomography curve recorded from a patient in wakefulness is shown in FIG. 3, where x-axis represents time (s) and y-axis represents impedance signal.

The plethysmographic curve of brain impedance is achieved by applying a constant current of 50-800 µA between the upper and lowest electrodes on the scalp (as shown in FIG. 2). The current will seek the path with the lowest impedance, i.e. the blood filled arteries. Hence the more blood present the impedance will be lower and consequently the voltage as well. The voltage plethysmography of each heart-beat is a correlate to the brain volume per beat (BV). The voltage plethysmogram (VP) will show periodic fluctuations from which the heart rate (HR) can be detected.

The HR could also be detected from the ECG 15 and the two compared to assure correct performance. From BV and HR the blood flow per minute (BF) can be computed by $$BF=HR\times BV \quad (2)$$

The range of BF is 0 to 10 l/min, while the normal physiological range is 1 to 6 l/min.

The impedance is measured in the range 5-300 000 Hz and used for both indices qCON and qNOX. With periodic intervals the mean impedance between electrodes and skin is measured. This is done in a low frequency range, typically 70 Hz. In the present invention the impedance curve is passive, which means it does not change with stimuli. The plethysmographic curve is averaged over a time window, for example 10 s, and this value, typically 20-50 Ohm, is used as an input to the processing module. If the impedance is high, that is above 10 KOhm, then typically more artifacts occur and compensation in the qCON index should be made. A continuous measurement of the impedance is carried out at a frequency in the range of 10-100 KHz, typically at 50 KHz.

Figure 4:
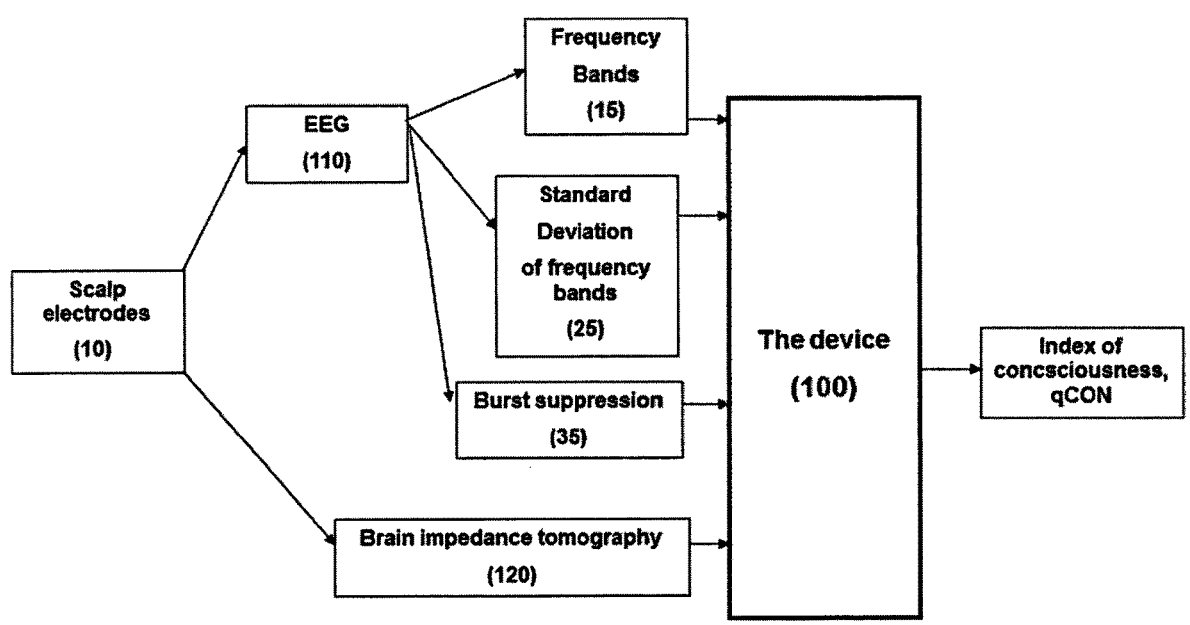
FIG. 4 is a schematic illustration of output of the index of consciousness qCON.

According to another embodiment of the present invention, the qCON algorithm was developed using four EEG frequency ratios (15), the burst suppression rate (35) and the standard deviation (25) of EEG spectral ratios over a time window (e.g. 10 s) as shown in FIG. 4. The EEG spectral ratios were fed into an Adaptive Neuro Fuzzy Inference System (ANFIS) or a quadratic equation. A reference scale was developed based on the OAAS scale and the Ramsay scale. The effect site concentrations of drug(s) (e.g. propofol and remifentanil) and the end tidal concentration of the volatile gases are used as a consistency control, i.e. data where the OAAS or Ramsay level indicates a different state (awake vs anaesthetized) than what is expected from the anaesthetics concentrations, are rejected and not used in the training of the model. The ANFIS model is trained using the spectral ratios, the burst suppression and the standard deviation as input while the reference clinical scale was the output. The BSR is the percentage of near isoelectric EEG in a window of 30s. Both suppression and bursts should have duration of more than 1 s in order to add up to the final BS count, detected by a Maximum-Likelihood algorithm. The frequency ratios are calculated every second, thus the qCON is updated every second. An exponential moving average has been applied in order to smooth rapid transitions. Assuming no artifacts in the EEG, the fifty percent update time of qCON is 5 s. The frequency ratios are defined in the following equation:

$$Frequency_n = 20 \times \log\frac{E_n}{E_{tot}} \quad (3)$$

where
$E_{tot}=E(1-44\ Hz)$
$E_1=E(4-8\ Hz)$
$E_2\ E(8-13\ Hz)$
$E_3=E(11-22\ Hz)$
$E_4=E(33-44\ Hz)$ The index qCON is defined as a combination of EEG spectral and EEG time parameters, the brain impedance tomography data is added as an input as well as shown in FIG. 4.

Figure 5:
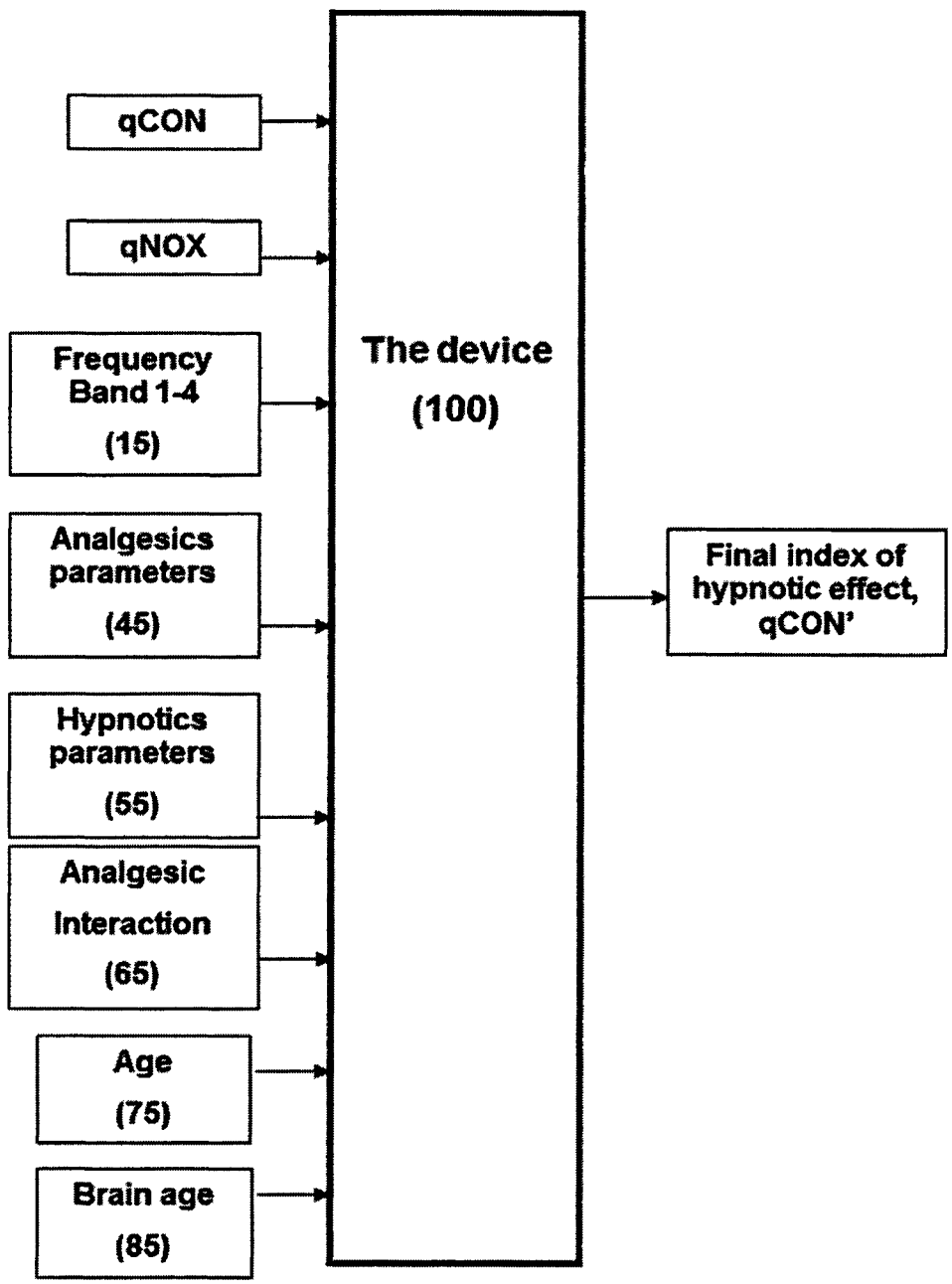
FIG. 5 is a schematic illustration of output of the final index qCON'.

The reference is now made to FIG. 5, which shows the flow chart of the final version of qCON, termed qCON'. The main parameter is qCON, which is then optimized by other parameters including frequency bands (15), analgesics parameters (45), hypnotics parameters (55), analgesic interaction (65), age (75) and brain age (85) as shown in FIG. 5. Item 15 are additional frequency bands. qNOX is used to compensate the qCON'. The items 45 to 65 are all related to the drug interactions, for example, pharmacokinetics and pharmacodynamics of the hypnotic drug (e.g. propofol) and the analgesic drug (e.g. remifentanil). The interaction between the drugs is typically defined by using an ANFIS model. The age (75) and brain age (85) are input as well. The EEG mean behavior changes with age that is why age is an input. However, there is an interpersonal variation of the alpha waves, and potentially other EEG bands, i.e., the subject might be 40 years old but his alpha waves while awake corresponds to a subject of 50 years old. The brain age is used to correct for this variation. So the value of brain age is also used as an input to the processing module. These parameters are combined to produce the final index qCON' by using ANFIS model, linear logistic regression, quadratic equations or other algorithms known in the state of the art.

Figure 6A:
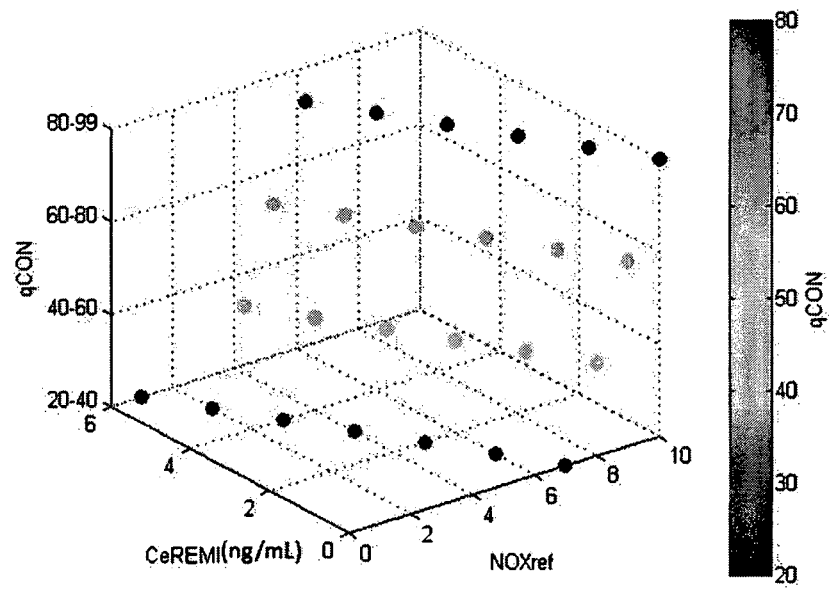
FIG. 6a shows the reference scale, NOXref, of qNOX without compensation for response to noxious stimulation.

According to another embodiment of the present invention, the index of nociception qNOX is developed by fitting the EEG data to a reference scale similar to qCON. The reference scale is composed of the index of consciousness qCON, the concentrations of infused drug (in this case, remifentanil) and response or lack of response to noxious stimulation such as tracheal intubation, Laryngeal mask airway (LMA) insertion or incision as shown in FIGS. 6a and 6b.

The reference is defined as the following:
If qCON≤20, then $NOX_{ref}=0$;
If 20<qCON≤40, then $NOX_{ref}=1$;
If 40<qCON≤60, then $NOX_{ref}=2$;
If 60<qCON≤80, then $NOX_{ref}=3$;
If 80<qCON≤100, then $NOX_{ref}=4$.

The effect site concentration of remifentanil (CeREMI) is added afterwards, $$NOX_{ref}=NOX_{ref}+6-CeREMI$$

Figure 6B:
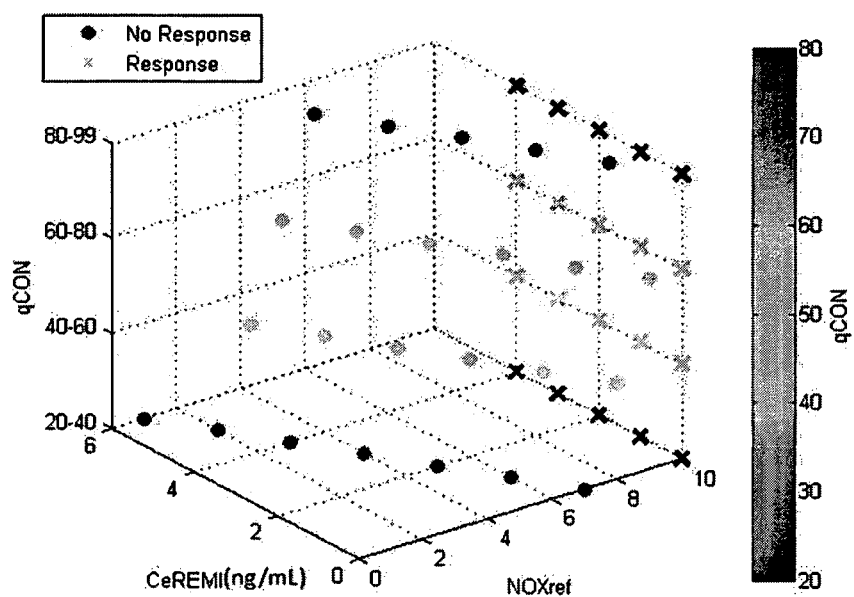
FIG. 6b shows the reference scale; NOXref, of qNOX with compensation for response to noxious stimulation. The crosses indicate the value of NOXref when the patient responds to noxious stimulation.

If the patient responds to a noxious stimulation (for example, moves after noxious stimulation), then $NOX_{ref}=10$ for a period of 1 minute after the noxious stimulation FIG. 6b. Otherwise, $NOX_{ref}$ remains unchanged as shown in FIG. 6a.

The $NOX_{ref}$ is then transformed to the 0 to 100 scale:

$$NOX_{ref}=NOX_{ref}\times 10$$

Figure 7:
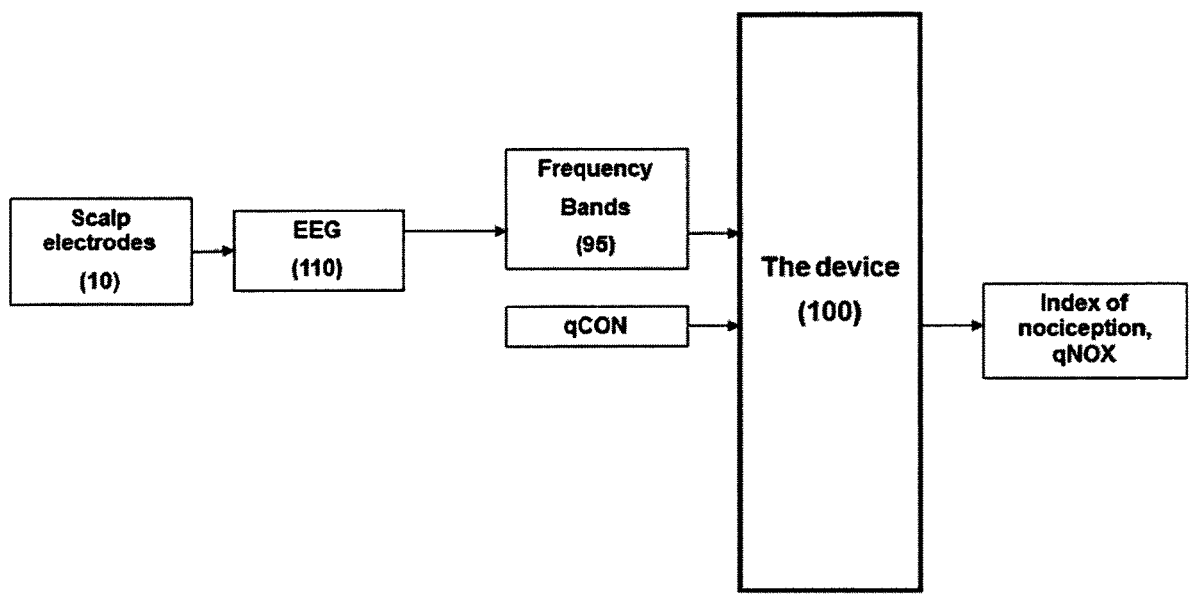
FIG. 7 is a schematic illustration of output of the index of nociception qNOX.
Figure 8:
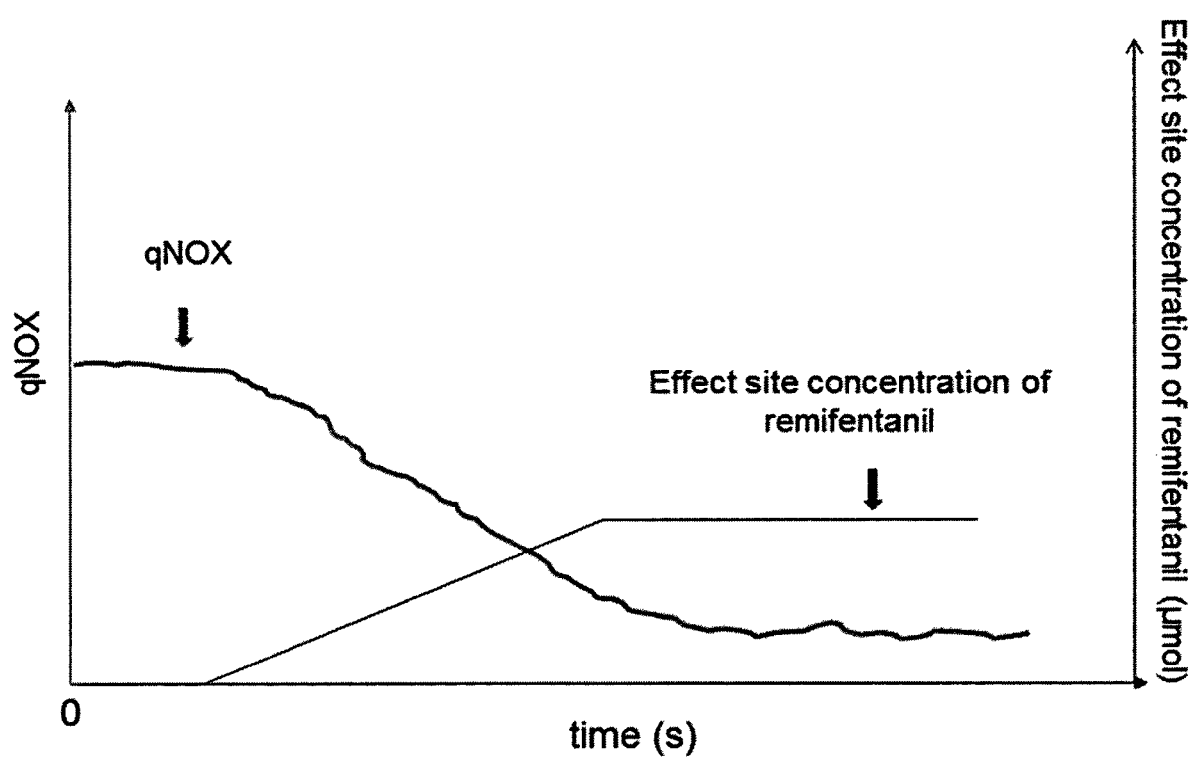
FIG. 8 exemplary illustrates an evolution of qNOX during infusion of an analgesic.

According to another embodiment of the present invention, the input to the qNOX model includes the 4 frequency ratios (95), ranging from 1 to 44 Hz. The qNOX is compensated by qCON as shown in FIG. 7. If qCON is below 25, it is assumed that the patient is in such deep anaesthesia state that response to noxious stimulation is unlikely. The qNOX uses equation (3) as described for calculation of qCON. The denominator Eta is the same, but the four frequency ratios (95) are different. For example, the frequency ratios below are used:
$E_5=E(1-8\ Hz)$
$E_6=E(8-13\ Hz)$
$E_7=E(21-26\ Hz)$
$E_8=E(30-44\ Hz)$ According to another embodiment of the present invention, qNOX changes alongside with the effect site concentration of analgesics. FIG. 8 shows that changes in the index qNOX correlate to change of the effect site concentration of remifentanil, an analgesic. The x-axis denotes time while the y-axis denotes qNOX in the range of 0 to 100 and the effect site concentration of remifentanil. When no analgesics are administered to the patient, the value of qNOX is high, indicating that the patient has a high probability of responding to noxious stimuli, leading to haemodynamic complications as myocardial infarction or stroke. When the remifentanil starts to take effect, then the qNOX drops to a lower value, indicating less probability of response to a noxious stimulus. However, a very strong noxious stimulus might cause the qNOX to increase although analgesia has been administered.

Figure 9:
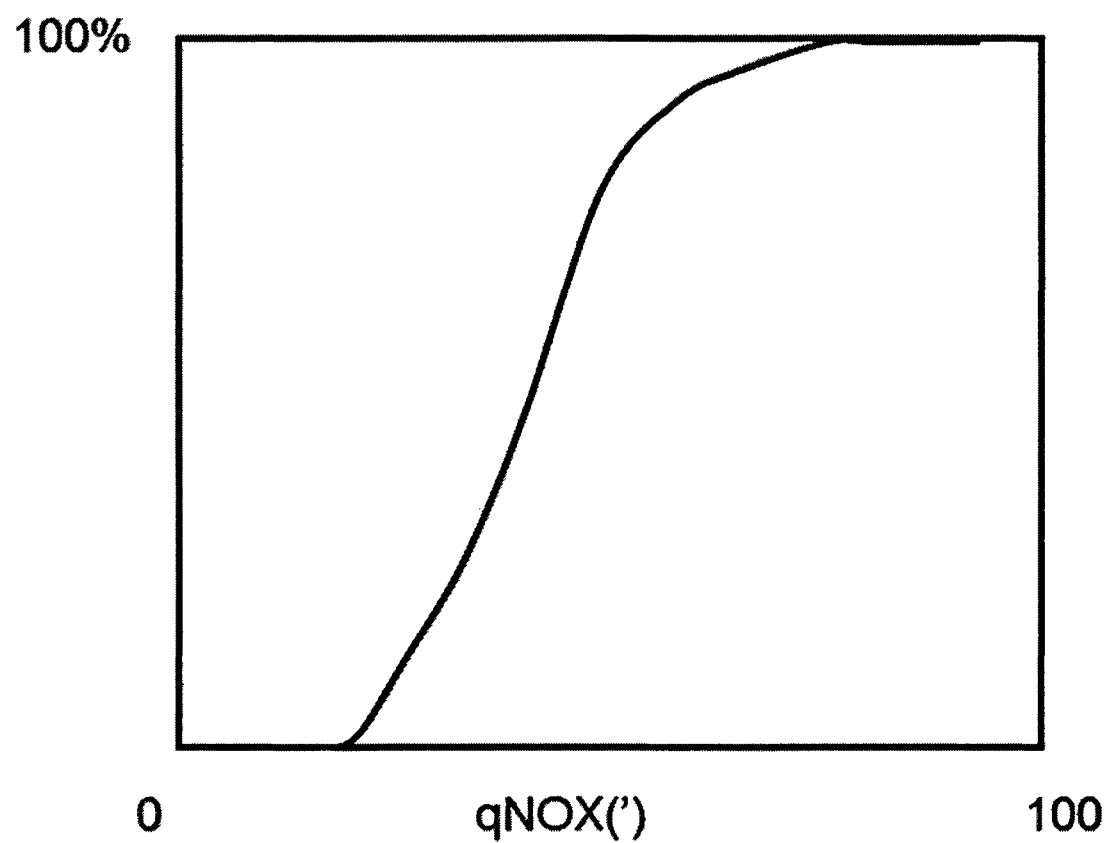
FIG. 9 is a sigmoid curve shows the conceptual relationship between qNOX(') and the probability of response to a noxious stimulus.

According to another embodiment of the present invention, the range of the qNOX is 0 to 100 corresponding to the probability of response to noxious stimuli following a sigmoid shaped logistic regression as shown in FIG. 9. qNOX at a value of 100 corresponds to a probability of response to noxious stimuli close to 100%. In contrast, qNOX at a value of 0 corresponds to a total block of noxious stimuli, which could be obtained by local anaesthetic drugs or high concentrations of analgesics (e.g. remifentanil).

Figure 10:
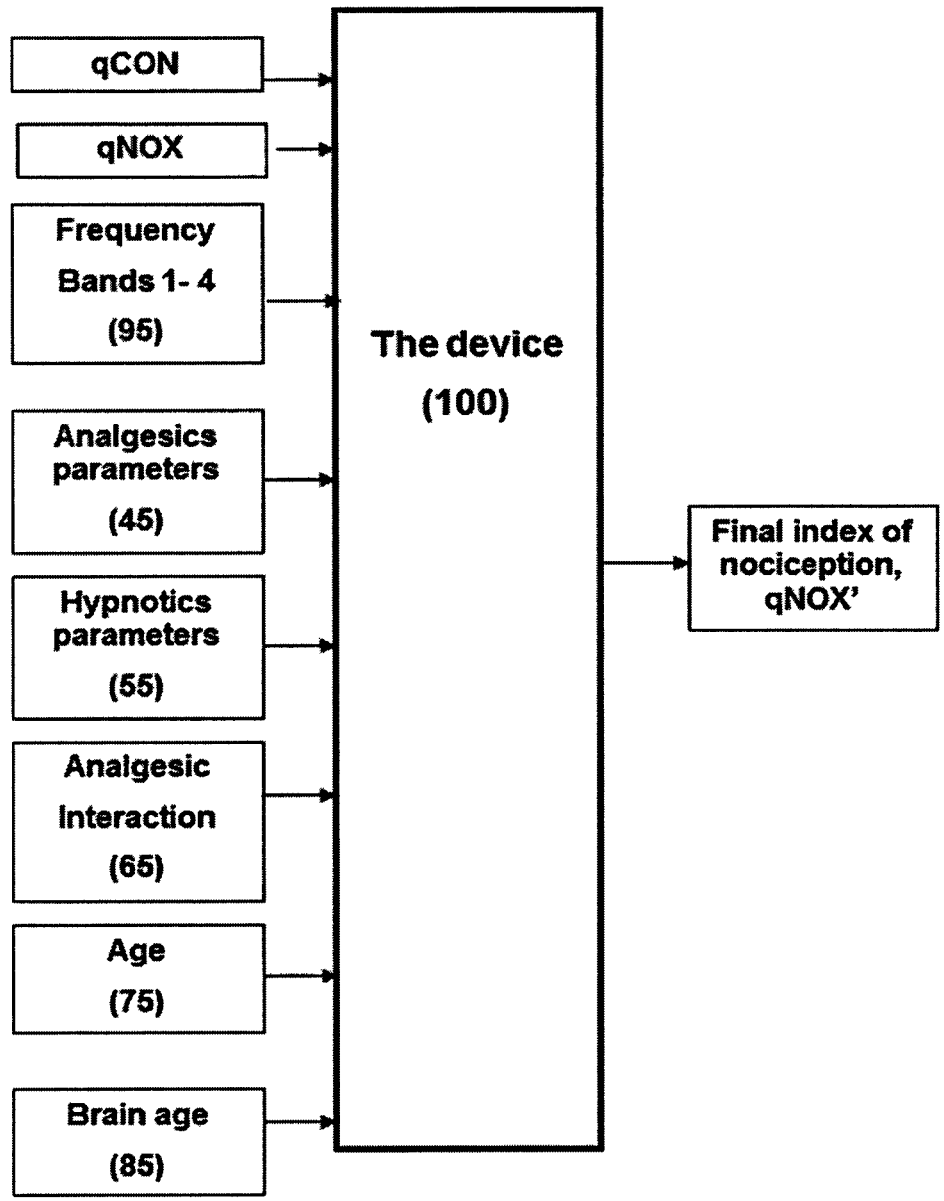
FIG. 10 is a schematic illustration of output of the final index qNOX'.

Reference is now made to FIG. 10 shows the flow chart of final version of qNOX, termed qNOX'. qNOX' includes additional information such as analgesics parameters (45), hypnotics parameters (56), analgesic interaction (65), age (75) and brain age (85) as shown in FIG. 10. The reason for entering additional parameters is the same as for the qCON. For both qCON' and qNOX' no underlying formula is used, the relationship is governed by the training data.

The optimal formula for defining the output, the qCON' and the qNOX', are obtained by training the model, with data where both the input and the output are known. This is a data driven approach with no underlying function governing the relationship between input and output.

According to another embodiment of the present invention, the least mean square (LMS) difference between the pain level assessed by the drugs concentration (pharmacodynamics=PD) and the pain level assessed by the qNOX is calculated. The LMS difference between the hypnotic effect assessed by the drugs concentration (pharmacodynamics=PD) and the hypnotic effect assessed by the qCON is provided as well. This could be expressed as:

$$LMS_{pain\ level}=\Sigma_{t=1}^{N}(qNOX_t-PDpain_t)^2 \qquad (4)$$

$$LMS_{hyp}=\Sigma_{t=1}^{N}(qCON_t-PDhyp_t)^2 \qquad (5)$$

Where PDpain is the pain level assessed by the pharmacodynamics, PDhyp is the hypnotic effect assessed by the pharmacodynamics of the drugs administered to the patient. The resulting LMS difference is sent to a warning module configured for activating an alarm if said LMS is greater than set threshold.

Figure 11:
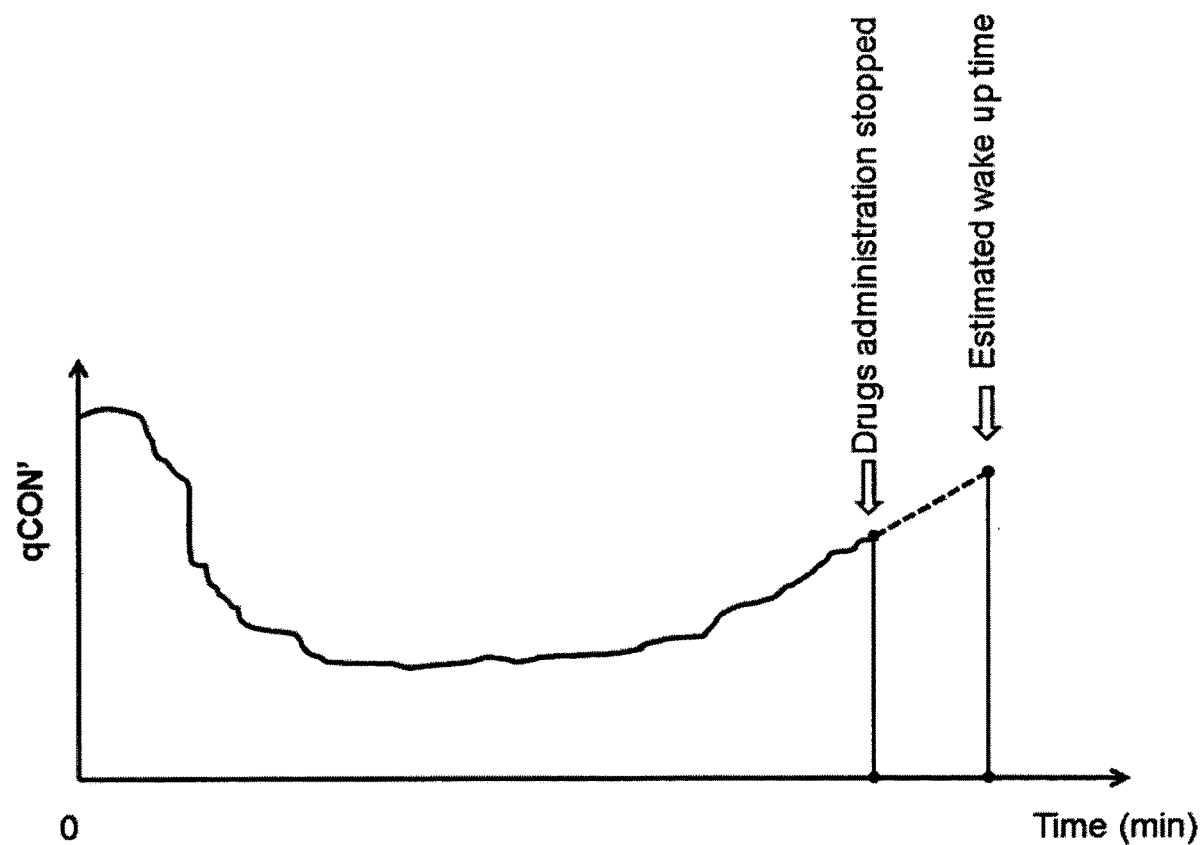
FIG. 11 exemplary illustrates an estimation of wake-up time based on the index qCON'.

According to another embodiment of the present invention, prediction of wake up time after the anaesthetics have been stopped, which is a useful parameter for the anaesthesiologist for the further planning of the patient flow, is provided. This is accomplished by the average slope of the qCON'. By estimating the slope over a time window, the time until qCON' is above a certain threshold can be calculated, as shown in FIG. 11, where x-axis represents time and y-axis represents qCON' in the range of 0 to 100.

The qCON and qNOX could be calculated according to the quadratic equation as shown below, $$Output = Intercept + \sum_{i} a_{1,i}*Input_i + \sum_{i} a_{2,i}*Input_i^2 + \sum_{i,j>i} a_{3,ij}*Input_i*Input_j$$

Where i,j=1 to 6; $a_1$=Linear coefficients; $a_2$=Quadratic coefficients; and $a_3$=Interaction coefficients The model structure can be seen in FIGS. 13 and 14.

The EOG is an abbreviation of Electrooculogram, which can be calculated as the amount of peaks that are above a certain amplitude threshold in a window of EEG.

The invention claimed is:

1. A device for assessing in real time the hypnotic and analgesic effect of one or more drugs infused in a subject during wakefulness, sedation and general anesthesia, comprising, at least one processor and at least one computer readable medium coupled to the processor, said at least one computer readable medium comprises operations executed by said at least one processor, said operations are:
   a. receiving electroencephalography (EEG) data from a plurality of electrodes positioned on the forehead of the subject;
   b. receiving brain impedance tomography data on the state of brain function from a brain impedance tomography device;
   c. receiving drug interaction data of the one or more drugs infused in said subject;
   d. defining an initial index of nociception (qNOX) as a function of said EEG data and said brain impedance tomography data;
   e. providing final index of nociception (qNOX');
   wherein said processor is configured to calculate said final index of nociception (qNOX') in real time using established mathematical manipulation from input of said EEG data and said drug interaction data.

2. The device according to claim 1, wherein said brain impedance tomography is measured from brain impedance tomography data received from the same electrodes receiving said EEG which are positioned on said subject's forehead.

3. The device according to claim 1, wherein qNOX is derived from a function of at least one parameter selected from any one or combination of the following which are based on said EEG data and said brain impedance tomography data: EEG spectra, energy ratios extracted by a fast Fourier transform, standard deviation of energy in EEG frequency band, rate of burst suppression, or brain impedance plethysmographic curve.

4. The device according to claim 1 wherein said one or more infused drugs has a group of effects consisting of: anesthetic, hypnotic, analgesic, or any combination thereof.

5. The device according to claim 1 wherein said drug interaction data including a group consisting of: pharmacokinetic data, pharmacodynamic data or any combination thereof.

6. The device according to claim 1 wherein said mathematical manipulation is selected form a group consisting: a linear regression, a quadratic equation, a logistic regression, a fuzzy logic classifier, a neural network, an Adaptive Neuro Fuzzy Inference System (ANFIS) or any combination thereof.

7. The device according to claim 1 wherein a value of the nociception index qNOX' varies from 0 to 100, corresponding to a probability of response to noxious stimuli.

8. The device according to claim 1 wherein the final index qNOX' is optimized from qNOX, by including a group of parameters consisting of: analgesics parameters, hypnotics parameters, analgesic interaction, age, brain age or any combination thereof.

9. The device according to claim 1 further comprising a reference scale developed based on a group consisting of: the Observers Assessment of Alertness and Sedation (OAAS), scale, the Ramsey Sedation Scale scale, effect site concentration of the one or more infused drugs, end tidal concentration of the volatile gases of the one or more infused drugs, response or lack of response to noxious stimulation or any combination thereof.

10. The device according to claim 1 further comprising a warning module configured for activating an alarm if the least mean square (LMS) difference between the hypnotic or analgesic effect assessed by the pharmacodynamics (pharmacodynamics=PD) of the one or more infused drugs and that assessed by qNOX is greater than set threshold; said LMS is expressed as:

$$LMS_{pain\ level} = \sum_{t=1}^{N} (qNOX_t - PDpain_t)^2$$

$$LMS_{hyp} = \sum_{t=1}^{N} (qCON_t - PDhyp_t)^2$$

where $PD_{pain}$ is the pain level assessed by the pharmacodynamics, $PD_{hyp}$ is the hypnotic effect assessed by the pharmacodynamics of the one or more infused drugs administered to the patient.

11. The device according to claim 1 wherein additionally an initial index of consciousness (qCON) as a function of said EEG data and said brain impedance tomography data is defined and a final index of consciousness (qCON') is provided, wherein said processor is also configured to calculate said final index of consciousness (qCON') in real time using established mathematical manipulation from input of said EEG data and said drug interaction data.

12. A method for assessing in real time the hypnotic and analgesic effect of one or more drugs infused in a subject during wakefulness, sedation and general anesthesia, comprising steps of:
   a. receiving electroencephalography (EEG) data from a plurality of electrodes positioned on the forehead of the subject;
   b. receiving brain impedance tomography data on the state of brain function from a brain impedance tomography device;
   c. receiving drug interaction data of the one or more drugs infused in said subject;
   d. defining an initial index of nociception (qNOX) as a function of said EEG data and said brain impedance tomography data;
   e. providing final index of nociception (qNOX');
   wherein said final index of nociception (qNOX') is calculated in real time via at least one processor using established mathematical manipulation from input of said EEG data and said drug interaction data.

13. The method of claim 12, wherein additionally an initial index of consciousness (qCON) as a function of said EEG data and said brain impedance tomography data is defined and a final index of consciousness (qCON') is provided, wherein said processor is also configured to calculate said final index of consciousness (qCON') in real time using established mathematical manipulation from input of said EEG data and said drug interaction data.

* * * * *